US00PP17989P2

(12) United States Plant Patent
Hoogendoorn

(10) Patent No.: US PP17,989 P2
(45) Date of Patent: Sep. 4, 2007

(54) ***ALSTROEMERIA* PLANT NAMED 'ZALSACHAP'**

(50) Latin Name: *Alstroemeria hybrida*
Varietal Denomination: Zalsachap

(75) Inventor: Cornelis Arie Hoogendoorn, Rijsenhout (NL)

(73) Assignee: Van Zanten Plants, B.V., Rijsenhout (NL)

( * ) Notice: Subject to any disclaimer, the term of this patent is extended or adjusted under 35 U.S.C. 154(b) by 0 days.

(21) Appl. No.: 11/255,209

(22) Filed: Oct. 20, 2005

(51) Int. Cl.
*A01H 5/00* (2006.01)

(52) U.S. Cl. ..... Plt./309
(58) Field of Classification Search ..... Plt./309
See application file for complete search history.

(56) References Cited

PUBLICATIONS

Upov–rom GTITM, Plant Variety Database, 2006/01, GTI Jouve Retrieval Software, Citation for Alstroemeria 'Zalsachap' one page.*

Van Zanten Plants B.V. [online], [retrieved on Nov. 15, 2006]. Retrieved form the Internet <http://www.royal-vanzanten.com/> 3 pages.*

* cited by examiner

*Primary Examiner*—Kent Bell
*Assistant Examiner*—June Hwu
(74) *Attorney, Agent, or Firm*—C. A. Whealy

(57) ABSTRACT

A new and distinct cultivar of *Alstroemeria* plant named 'Zalsachap', characterized by its erect and strong flowering stems; vigorous growth habit; intense red purple and yellow-colored flowers; and good postproduction longevity.

1 Drawing Sheet

Botanical designation: *Alstroemeria hybrida.*
Cultivar denomination: 'Zalsachap'.

BACKGROUND OF THE INVENTION

The present Invention relates to a new and distinct cultivar of *Alstroemeria* plant, botanically known as *Alstroemeria hybrida,* commerically used as a cut flower *Alstroemeria,* and hereinafter referred to by the name 'Zalsachap'.

The new *Alstroemeria* is a product of a planned breeding program conducted by the Inventor in Rijsenhout, The Netherlands. The objective of the breeding program was to develop new cut flower *Alstroemeria* cultivars with desirable flower and plant qualities, attractive flower colors and excellent postproduction longevity.

The new *Alstroemeria* originated from a cross-pollination made by the Inventor in June, 1999 in Rijsenhout, The Netherlands, of a proprietary *Alstroemeria hybrida* selection identified as 90P506-1, not patented, as the female, or seed, parent with a proprietary *Alstroemeria hybrida* selection identified as 87F1459-1, not patented, as the male, or pollen, parent. The new *Alstroemeria* was discovered and selected by the Inventor as a flowering plant within the progeny of the stated cross-pollination in a controlled environment in Rijsenhout, The Netherlands.

Asexual reproduction of the new cultivar by root divisions in a controlled environment in Rijsenhout, The Netherlands, since August, 1999, has shown that the unique features of this new *Alstroemeria* are stable and reproduced true to type in successive generations of asexual propagation.

SUMMARY OF THE INVENTION

Plants of the cultivar Zalsachap have not been observed under all possible environmental conditions. The phenotype may vary somewhat with variations in environment such as temperature and light intensity without, however, any variance in genotype.

The following traits have been repeatedly observed and are determined to be the unique characteristics of 'Zalsachap'. These characteristics in combination distinguish 'Zalsachap' as a new and distinct cultivar:

1. Erect and strong flowering stems.
2. Vigorous growth habit.
3. Intense red purple and yellow-colored flowers.
4. Good postproduction longevity.

Plants of the new *Alstroemeria* can be compared to plants of the female parent selection. In side-by-side comparisons conducted in Rijsenhout, The Netherlands, plants of the new *Alstroemeria* differed from plants of the female parent selection in the following characteristics:

1. Plants of the new *Alstroemeria* had larger flowers than plants of the female parent selection.
2. Plants of the new *Alstroemeria* and the female parent selection differed in flower color as plants of the female parent selection had purple-colored flowers.

Plants of the new *Alstroemeria* can be compared to plants of the male parent selection. In side-by-side comparisons conducted in Rijsenhout, The Netherlands, plants of the new *Alstroemeria* differed primarily from plants of the male parent selection in flower color as plants of the male parent selection had orange-colored flowers.

Plants of the new *Alstroemeria* can also be compared to plants of the cultivar Stabec, disclosed in U.S. Plant Pat. No. 9,041. In side-by-side comparisons conducted in Rijsenhout, The Netherlands, plants of the new *Alstroemeria* differed from plants of the cultivar Stabec in the following characteristics:

1. Plants of the new *Alstroemeria* had shorter flowering stems than plants of the cultivar Stabec.

2. Plants of the new *Alstroemeria* had broader leaves than plants of the cultivar Stabec.
3. Plants of the new *Alstroemeria* and the cultivar Stabec differed in flower color as plants of the cultivar Stabec had red and white-colored flowers.

BRIEF DESCRIPTION OF THE PHOTOGRAPH

The accompanying colored photograph illustrates the overall appearance of the new *Alstroemeria,* showing the colors as true as it is reasonably possible to obtain in colored reproductions of this type. Colors in the photograph may differ slightly from the color values cited in the detailed botanical description which accurately describe the colors of the new *Alstroemeria.* The photograph comprises a side perspective view of a typical flowering stem of 'Zalsachap'.

DETAILED BOTANICAL DESCRIPTION

The aforementioned photograph and following observations and measurements describe plants of the new *Alstroemeria* grown in Rijsenhout, The Netherlands in a glass-covered greenhouse in ground beds. During the production of the plants, day temperatures ranged from 15° C. to 20° C., night temperatures ranged from 10° C. to 15° C., soil temperature was about 14° C. and light levels averaged 5,000 lux. Plants used for the photograph and description were about one year-old. The photograph and the description were taken during March and April, 2005. Color references are made to The Royal Horticultural Society Colour Chart, 1995 Edition, except where general terms of ordinary dictionary significance are used.

Botanical classification: *Alstroemeria hybrida* cultivar Zalsachap.

Parentage:

*Female parent.*—Proprietary *Alstroemeria hybrida* selection identified as 90P506-1, not patented.

*Male parent.*—Proprietary selection of *Alstroemeria hybrida* identified as 87F1459-1, not patented.

Propagation:

*Type.*—By root divisions.

*Root description.*—Fibrous, fleshy, thick; white, close to 155D, in color.

*Rooting habit.*—Freely branching.

*Rhizomes.*—Shape: Elongate; rounded. Length: About 10 cm to 30 cm. Diameter: About 3 mm to 10 mm. Texture: Smooth. Color: Close to 155D.

Plant description:

*Plant habit.*—Upright; freely branching, bushy appearance. Vigorous growth habit.

*Time from planting to harvest of cut flowers.*—About 80 to 90 days.

*Number of flowering stems produced per year.*—About 200 to 220.

*Plant height.*—About 140 cm to 180 cm.

*Plant diameter (spread).*—About 25 cm to 30 cm.

*Flowering stem description.*—Aspect: Erect. Length: About 120 cm. Diameter: About 8 mm to 10 mm. Internode length: About 1 cm to 5 cm. Strength: Strong. Texture: Smooth, glabrous. Color: Close to 143A.

*Foliage description.*—Leaves simple and asymmetrical; sessile. Length: About 15 to 20 cm. Width: About 4 cm to 5 cm. Shape: Lanceolate. Apex: Acute. Base: Attenuate. Margin: Entire. Texture, upper and lower surfaces: Smooth, glabrous. Venation pattern: Parallel. Color: Developing and fully developed foliage, upper surface: Close to 141A; slightly glossy; venation, similar to lamina. Developing and fully developed foliage, lower surface: Close to 141B; venation, similar to lamina.

Flower description:

*Flower type and habit.*—Single cup-shaped flowers arranged in compound umbels. Perianth segments separate. Freely and continuously flowering. Flowers not persistent.

*Natural flowering season.*—Flowering continuous during the spring in The Netherlands.

*Fragrance.*—None detected.

*Flower longevity on the plant.*—About four weeks.

*Flower longevity as a cut flower.*—About 20 to 25 days.

*Flower buds (showing color).*—Length: About 3 cm to 4 cm. Diameter: About 1 cm to 2 cm. Shape: Roughly ovoid. Color: 59A.

*Umbel length.*—About 15 cm to 20 cm.

*Umbel diameter.*—About 20 cm to 25 cm.

*Number of flowers per umbel.*—About 20 to 30.

*Flower diameter.*—About 7 cm to 8 cm.

*Flower length (height).*—About 8 cm to 9 cm.

*Flower depth.*—About 5 cm to 6 cm.

*Perianth.*—Arrangement: Six arranged in two whorls, each whorl with two lateral and one median segments. Outer perianth: Length, lateral segments: About 6 cm to 7 cm. Width, lateral segments: About 2.5 cm to 3.5 cm. Length, median segment: About 6 cm to 7 cm. Width, median segment: About 3 cm to 4 cm. Shape, lateral and median segments: Obovate. Apex, lateral and median segments: Pointed. Base, lateral and median segments: Attenuate. Margin, lateral and median segments: Entire; weakly undulate. Texture, lateral and median segments: Smooth, glabrous; velvety. Color, lateral segments, when opening and fully opened, upper surface: 53C; apical tip, close to 144A. Color, lateral segments, when opening and fully opened, lower surface: 53D; apical tip, close to 144A. Color, median segment; when opening and fully opened, upper surface: 53C; apical tip, close to 144A. Color: median segment; when opening and fully opened, upper surface: 53D; apical tip, close to 144A.

*Inner perianth.*—Length, lateral segments: About 6 cm to 7 cm. Width, lateral segments: About 1.5 cm to 2.5 cm. Length, median segment: About 5 cm to 6 cm. Width, median segment: About 1.5 cm to 2 cm. Shape, lateral and median segments: Oblanceolate. Apex, lateral and median segments: Acute. Base, lateral and median segments: Attenuate. Margin, lateral and median segments: Entire; weakly undulate. Texture, lateral and median segments: Smooth, glabrous; velvety. Color, lateral segments, when opening and fully opened, upper surface: Towards the base, 4A; towards the apex, 53C; apical tip, close to 4D; stripes, close to 59A. Color, lateral segments, when opening and fully opened, lower surface: 53D; apical tip, close to 4D. Color, median segment, when opening and fully opened, upper surface: 53C; apical tip, close to 4D; stripes, close to 59A. Color, median segment, when opening and fully opened, lower surface: 53D; apical tip, close to 4D.

*Peduncles.*—Length: About 9 cm to 18 cm. Diameter: About 3 mm to 4 mm. Strength: Strong. Angle: About 10° to 20° from vertical. Texture: Smooth, glabrous. Color: Close to 141A.

*Pedicels.*—Length: About 1 cm to 3 cm. Diameter: About 3 mm to 4 mm. Strength: Strong. Angle: About 10° to 20° from vertical. Texture: Smooth, glabrous. Color: Close to 141A.

*Reproductive organs.*—Stamens: Quantity per flower: Six. Anther shape: Elliptical. Anther length: About 9 mm. Anther diameter: About 3 mm. Anther color: Close to 177A. Filament length: About 3.7 cm to 4.5 cm. Pollen amount: Scarce. Pollen color: Close to 79A. Pistils: Quantity per flower: One. Style length: About 3.5 cm to 4 cm. Style color: Towards the apex, 59C; towards the base, 62C. Stigma color: 59D. Ovary color: Close to 147A.

*Fruit.*—Quantity of fruit per plant: Few. Shape: Globular. Color: Upper surface, 147A; lower surface, 137C. Size: About 8 mm by 6 mm.

Disease/pest resistance: Plants of the new *Alstroemeria* have not been observed to be resistant to pathogens and pests common to *Alstroemerias.*

Temperature tolerance: Plants of the new *Alstroemeria* have been observed to tolerate temperatures from −5° C. to 40° C.

It is claimed:

1. A new and distinct cultivar of *Alstroemeria* plant named 'Zalsachap', as illustrated and described.

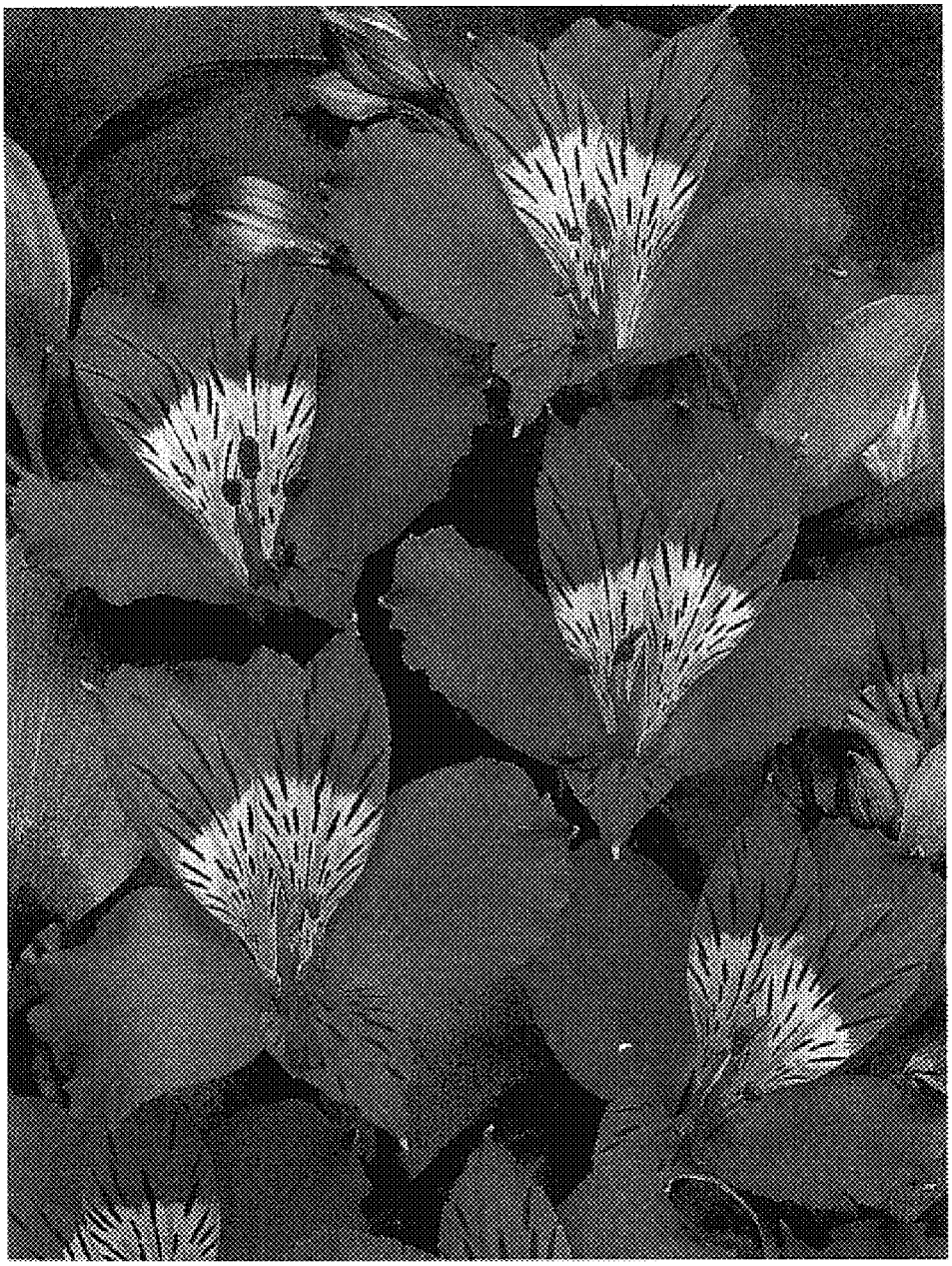

* * * * *